(12) United States Patent
Shannon

(10) Patent No.: US 6,793,897 B2
(45) Date of Patent: Sep. 21, 2004

(54) BIOLOGICAL AND CHEMICAL DEFENSE APPARATUS UTILIZING COLD PLASMA GENERATED PRESSURIZED ACTIVATED OXYGEN

(76) Inventor: John O. Shannon, 10716 - 59$^{th}$ Ave. North, Seminole, FL (US) 33772

( * ) Notice: Subject to any disclaimer, the term of this patent is extended or adjusted under 35 U.S.C. 154(b) by 320 days.

(21) Appl. No.: 10/100,329

(22) Filed: Mar. 18, 2002

(65) Prior Publication Data

US 2003/0175180 A1 Sep. 18, 2003

(51) Int. Cl.$^7$ ................................................ B01J 19/08
(52) U.S. Cl. .............. 422/186; 422/186.04; 422/186.07
(58) Field of Search ............................ 422/186, 186.04, 422/186.07

(56) References Cited

U.S. PATENT DOCUMENTS

| | | | |
|---|---|---|---|
| 3,549,528 A | 12/1970 | Armstrong | 210/60 |
| 4,640,782 A | 2/1987 | Burleson | 210/748 |
| 5,087,419 A | 2/1992 | Lutz | 422/28 |
| 5,472,664 A | 12/1995 | Campbell et al. | 422/23 |
| 5,752,878 A | 5/1998 | Balkany | 484/236 |
| 5,882,591 A | 3/1999 | Kekez | 422/28 |
| 6,228,330 B1 * | 5/2001 | Herrmann et al. | 422/186.05 |
| 6,284,193 B1 | 9/2001 | Carman et al. | 422/33 |

\* cited by examiner

*Primary Examiner*—Steven VerSteeg
(74) *Attorney, Agent, or Firm*—Larson & Larson, PA; James E. Larson

(57) ABSTRACT

A biological and chemical defense apparatus utilizing cold plasma, generated, pressurized, activated oxygen including a front and rear housing, each housing having its own internal cavity. The rear housing encloses a generator plate bed coupling to a cold plasma generator plate having an anode and cathode. The rear housing having a pair of ports, one for drawing air in and one for expelling pressurized, activated oxygen out. The front housing encloses a transformer and a pressure control switch connected to a power source. The rear housing inserts within an air duct on the supply side of an HVAC air handler with the front housing extending outwardly from an outer wall surface of the air duct, wherein pressurized air from the fan mixes with the activated oxygen created by the generator plates, therefore dispersing it through the duct system and treating the air to constant purification from contaminants.

28 Claims, 11 Drawing Sheets

BIOLOGICAL AND CHEMICAL DEFENSE APPARATUS UTILIZING COLD PLASMA GENERATED PRESSURIZED ACTIVATED OXYGEN

BACKGROUND OF THE INVENTION

1. Field of the Invention

This invention relates to indoor air quality improvement. More particularly, it relates to a device for improving the air quality of an indoor structure and defending it against biological and chemical contaminants through the use of pressurized activated oxygen created through a cold plasma generating device.

2. Description of Prior Art

Improving indoor air quality and the ability to defend an enclosed environment from biological and chemical contaminants has been addressed in the prior art. Much of the prior art has been developed due to a greater understanding that poor air quality in a contained environment can effect one's health resulting in serious sickness, and sometimes death, or at a minimum, irritating health side effects. The increasing costs of energy have resulted in stricter building codes which has resulted in tighter sealed indoor environments and poorer indoor air quality.

It is well known and documented that buildings can be inflicted with something referred to as "Sick Building Syndrome" (SBS) whereby inhabitants and occupants can manifest a multitude of varying symptoms from headaches, tiredness, nausea, dizziness, short-term memory loss, irritability, itchy eyes and throats and running noises to serious viral and bacteria inflictions and even Legionnaries Disease, a type of pneumonia which attacks 2–5% of those exposed thereto. It is further known that between 5–15% of those who contract legionella can die from exposure thereto. The elderly, the young and those having compromised or suppressed immune systems are at an even greater risk of contracting many of the symptoms and sicknesses known to be attributable to "Sick Building Syndrome." Tuberculosis, or TB, is a deadly bacteria which is transmitted through the air and is contracted in humans by inhalation. Again, the elderly, the young and those with a suppressed immune system are at an even greater risk of contracting TB if exposed thereto. Since mycobacterium tuberculosis is carried in airborne particles known as droplet nuclei, which are so small that they can be indefinitely suspended in the air, it is very easy for this dangerous bacteria to travel through the HVAC system of a commercial building or home. Addressing these dangerous bacteria and viruses, as well as simple molds and mildews, within enclosed environments is therefore of great importance in purifying an environment inflicted with the "Sick Building Syndrome", or other similar condition.

Another controversial disease associated with "Sick Building Syndrome" is "Multiple Chemical Sensitivity" (MCS), which can make people allergic to almost anything containing a man-made chemical. This condition can have devastating effects upon a person's immune system, sometimes forcing people to retreat to a surreal environment separated from the rest of the world by a "plastic bubble". The Environmental Protection Agency (EPA) has even gone as far to say that indoor air quality is one of the top five environmental health risks of the present time. Further, at the present time, almost a dozen states now recognize MCS as a bona fide claim for workers' compensation and is also covered on a case by case basis under the Americans with Disabilities Act, obliging employers to make accommodations for sufferers of the disease.

Along with the naturally occurring contaminants as described directly above, there is now a great need for defending against the deliberate contamination of enclosed environments with known toxins, be they made man or naturally occurring in nature, by criminals and terrorists, as well as accidental chemical spills. Although gas masks and filters may assist in thwarting an attack or accident occurring within an enclosed environment which would diminish some of the effects of the biological or chemical toxins, they do nothing for sterilizing the contaminated environment for re-habitation and re-occupancy. Further, since many of the known biological and chemical toxins and pathogens are relatively small in particle size, some even being odorless, filters and gas masks may prove to be ineffective if someone where exposed.

The use of ozone, an allotropic form of oxygen, has been known to be a powerful oxidant used in the sterilization of articles of manufacture. Ozone has been used for years to treat and sterilize biological fluids and medical instruments and to purify hospital environments. It has also been known to be useful in the treatment of industrial wastes for safe discharge. As shown in U.S. Pat. No. 5,882,591 to Kekez, biological fluids are treated with ozone having a composition of either an $O_3/O_2$ or an $O_3$/inert gas mixture. It is important to note that ozone as described is a combination of $O_3$ and another inert gas or oxygen composition. Prior to the invention described hereinafter, no one has taught the use of using merely the $O_3$ portion of ozone in a pressurized setting to treat and defend against mold, mildew, and other known irritants.

It is known that the use of highly pressurized, oxygenated environments can promote the healing of some sicknesses in people. Hyperbaric chambers are of course well known in the prior art for the treatment of decompression sickness for sport and commercial scuba divers who either exceed their "bottom time" of breathing compressed air or for those who ascend too quickly from a deep dive. Decompression sickness results from an elevated level of nitrogen in the blood stream, which has built up during a dive, and which can not escape quickly enough out of the blood stream and out through the skin of a person. The highly pressurized environment and elevated levels of oxygen within the hyperbaric chamber promotes the rapid evaporation (or release) of the elevated nitrogen from the person's body.

What has not been developed in the prior art, but is greatly needed, is a device which utilizes some of the attributes of a hyperbaric chamber as well as those of an ozone generator to treat and purify the air of an enclosed environment. A device which emits a pressurized form of $O_3$ is greatly needed. Such a device attached to the HVAC system of a home, school or commercial building could constantly purify and treat the air of the enclosed environment, under pressure, to rid it of mold, mildew and biological and chemical contaminants which lead to serious health complications. Such a device could also act as a defense mechanism for any contaminants introduced by accident or by purposeful design all the while being unobtrusive to the people inhabiting the area being treated. Prior to the invention herein, no such device exits.

SUMMARY OF THE INVENTION

I have invented a device for treating the air and contents of an enclosed environment which acts to kill and prohibit the future proliferation of mold and mildew and defend said environments against biological and chemical contaminants and toxins which may invade the environment by accident or by purposeful design. In its preferred form, the novel device of the present invention mounts to the supply side of a duct of a HVAC system. The device includes a series of cold plasma generator plates mounted within a housing which when charged with a low level voltage creates a source of activated oxygen ($O_3$). The specially designed generator plates drastically reduce the possibility of nitric oxide from being produced, which is known to destroy activated oxygen. The activated oxygen is then pressurized to a level above the ambient air pressure and introduced into the duct system of the HVAC system for distribution throughout the building associated therewith. The square footage area of the enclosure to be treated and the tonnage rating of the HVAC system dictates the number of generator plates to be employed within the device. It is also noted that the generator plates employed with the novel device of the present invention produces no heat, an advantage over known prior art ozone generators.

By introducing the activated oxygen ($O_3$) under pressure, all solid objects within the enclosure are penetrated and thereby treated for any and all contaminants on the surface of the object or embedded therein, which include, but is not limited to, the walls, furniture, clothes, carpets, drapes, and other typical household and office items and fixtures. The pressurized activated oxygen is completely safe to the respiratory system of humans and other animals and causes no harmful disruption to the environment being treated. The use of pressure also ensures that any unwanted chemicals or biological agents present in the air are prohibited from entering the environment by way of the ambient air due to the positive pressure pushing against any incoming ambient air. However, if any contaminants are brought in on a substrate, such as a shoe or piece of clothing, or exhaled from a person's body (i.e., coughing), it is immediately attacked by the continuous pressurized source of activated oxygen from the novel device of the present invention.

An alternate embodiment of the present invention includes a stand alone apparatus having a plurality of units enclosing the cold plasma $O_3$ generator plates. The stand alone apparatus attaches to a door or window for drawing in ambient air, thereafter treating the air to create the pressurized activated oxygen and thereafter dispersing said pressurized activated oxygen out through air ports for treating the enclosed environment. This alternate embodiment of the novel device can be used to quickly address enclosures that have been exposed, by accidental or by purposeful design, to airborne contaminants which are harmful to people to inhale or otherwise be exposed thereto. This alternate embodiment can also be used to treat sick buildings that are inflicted with mold and mildew behind the walls. This novel alternate embodiment has great use for insurance companies which hereto before would have to compensate its insured for the sick building and then have the building burned down to rid it completely of the mold and mildew or other irritant.

Yet another alternate embodiment includes a single unit attached to an air vent along a building hallway corridor. This alternate embodiment draws in ambient air from behind the building hallway corridor by a fan, creating a pressurized air source which is mixed with the activated oxygen ($O_3$) and thereafter dispersed through the air vent. This unit has great use for older buildings not employing central HVAC systems, like those found in many older schools and buildings which are built in environments which are not exposed to great heat and therefore typically do not need central HVAC systems.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
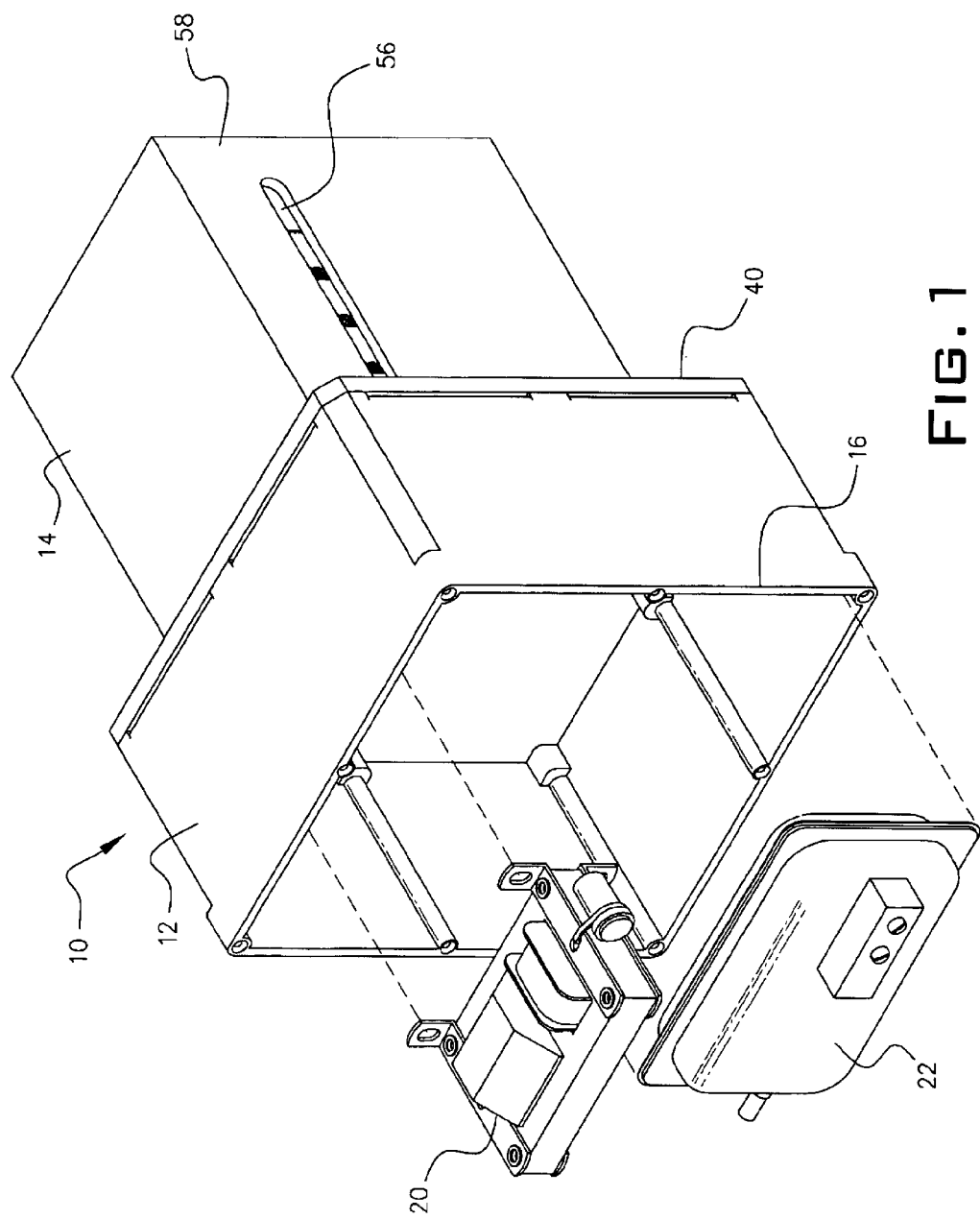
FIG. 1 is a front perspective view, partially exploded, of the biological and chemical defense apparatus utilizing cold plasma generated pressurized activated oxygen in its preferred form.

Throughout the following detailed description, the same reference numerals refer to the same elements in all figures.

Referring to FIG. 1, a biological and chemical defense apparatus 10 of the present invention is shown in a partially exploded view. Apparatus 10 has front and rear housing portions, 12 and 14 respectively, of which each have a generally square-shaped configuration. However, in its preferred form, front housing 12 is slightly larger in size as that of rear housing 14, although rear housing 14 has a greater depth along a center axis running from a front portion 16 of apparatus 10. Apparatus 10 also includes a lid portion 18, not shown in FIG. 1, but depicted in FIG. 7, which encloses electronic circuitry used with the novel apparatus 10 of the present invention.

Figure 2:
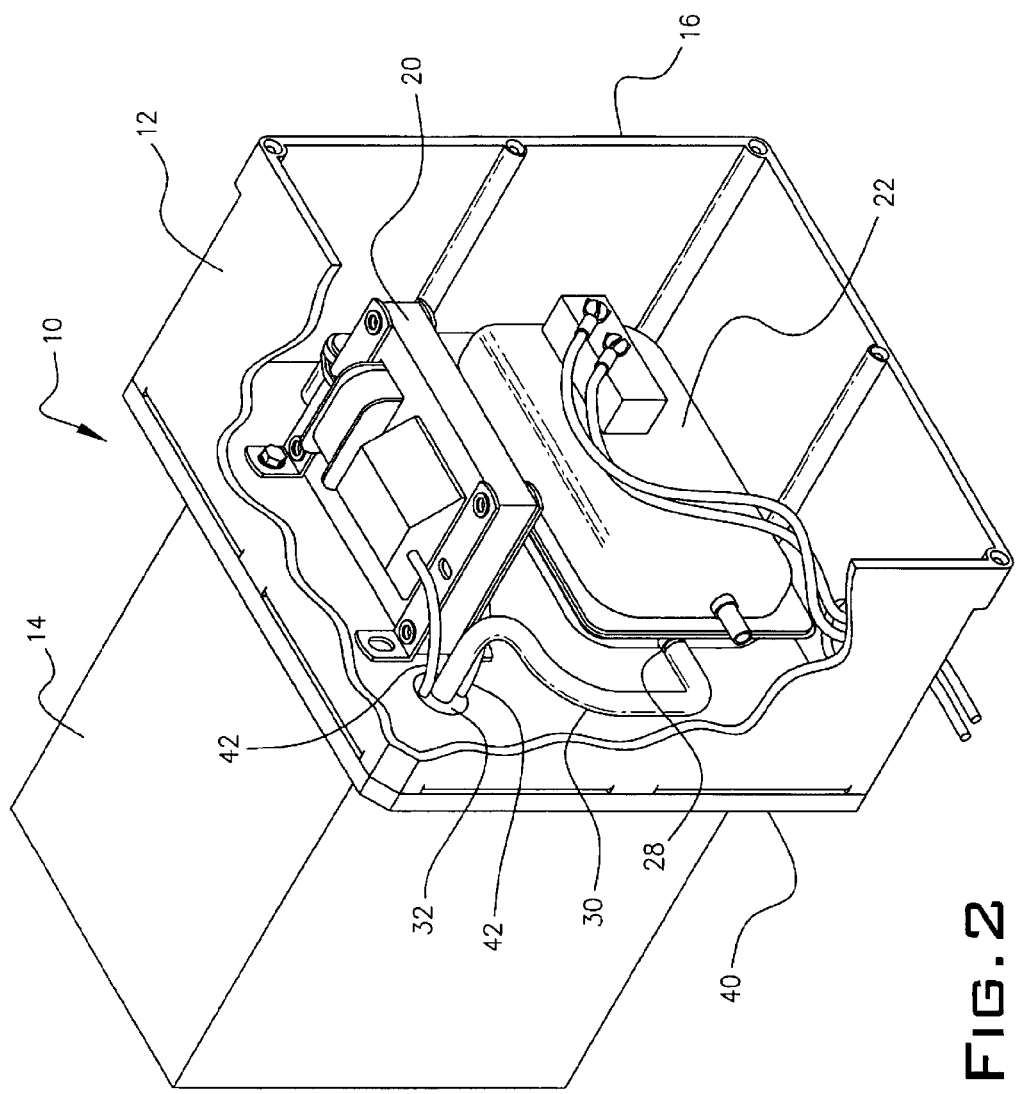
FIG. 2 is a perspective view, partially in section, of the apparatus depicted in FIG. 1.
Figure 11:
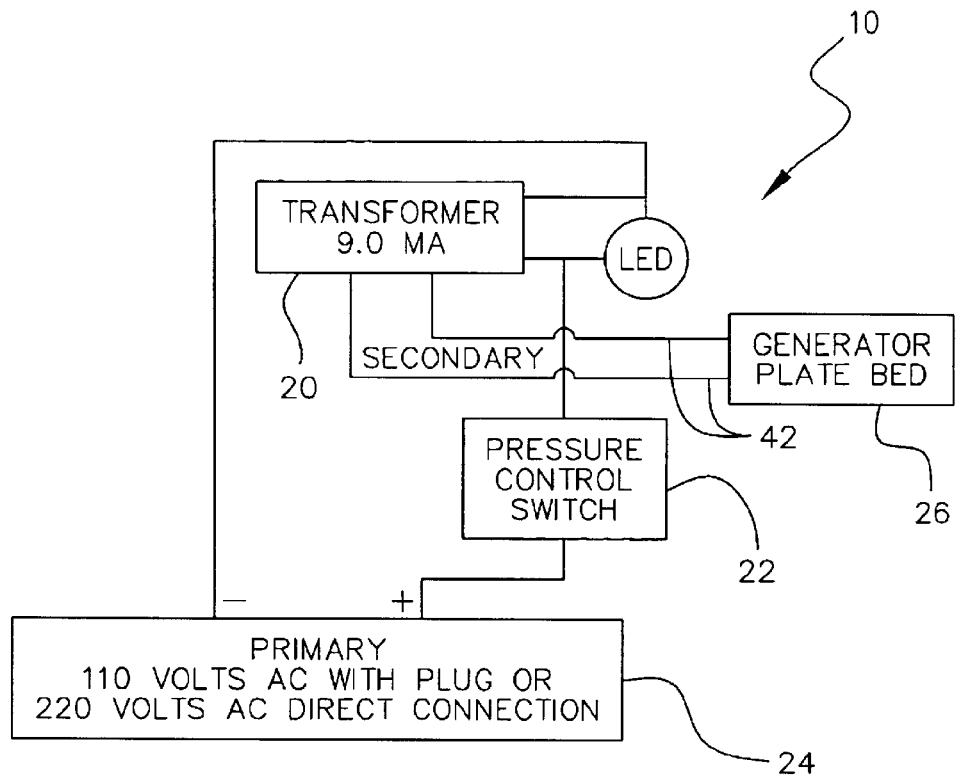
FIG. 11 is a schematic diagram of the circuitry employed in the preferred embodiment of the apparatus of the present invention.

With reference to both FIGS. 1 and 2, it is shown that apparatus front housing 12 encloses a transformer 20 and a pressure control switch 22. With reference to FIG. 11, an electrical schematic diagram, it is shown that both transformer 20 and pressure control switch 22 are coupled to a power source 24, such as a 110 volt AC plug or a 220 volt AC direct connection. As also shown in FIG. 11, an LED is provided for indicating an "on" state for apparatus 10 and is coupled to transformer 20, pressure switch 22 and power source 24. The LED is primarily used to indicate that apparatus 10 is properly working when first installed to its power source. As further shown, the secondary of transformer 20 is connected to a generator plate bed 26 which couples to at least one generator plate, not shown in FIG. 11, but which will be more fully discussed in further detail hereinafter.

Figure 3:
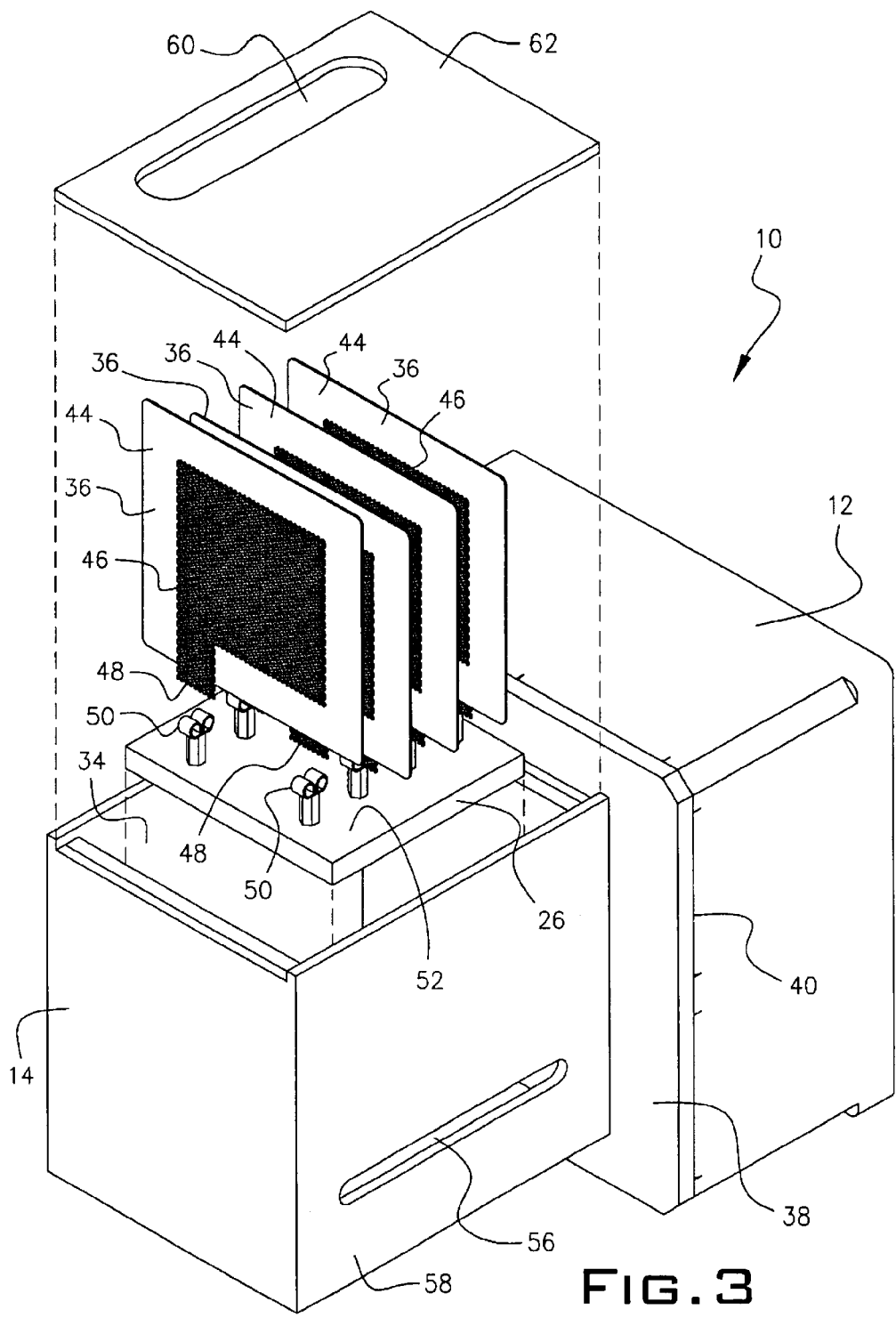
FIG. 3 is a rear perspective view, partially exploded, of the apparatus depicted in FIG. 1, illustrating how cold plasma generator plates are employed within a rear housing portion of the apparatus.

Referring to FIG. 2, it is shown that pressure control switch 22 has an outlet port 28 from which a flexible tube 30 is connected thereto. Flexible tube 30 inserts through a sealed opening 32 leading into an internal cavity 34 of apparatus rear housing 14 which supports generator plate bed 26 and a plurality of generator plates 36 which electrically couple to generator plate bed 26 (as shown in FIG. 3). In its preferred form, sealed opening 32 is sealed by tar paper.

With continuing reference to FIG. 3, it is shown that apparatus rear housing 14 mounts to a back side 38 of apparatus front housing 12. A layer of pliable insulating foam 40 is positioned between apparatus front and rear housings, 12 and 14 respectively. Foam 40 is used to insulate the two housings from one another thereby prohibiting any moisture or air exchange from one environment to the other of the two housings.

With reference to FIG. 11, it is shown that generator plate bed 26 connects by a pair of leads 42 to the secondary of transformer 20. As shown in FIGS. 2 and 3, leads 42 fish through sealed opening 32 and into rear housing internal cavity 34 for connection to generator plate bed 26.

Figure 5:
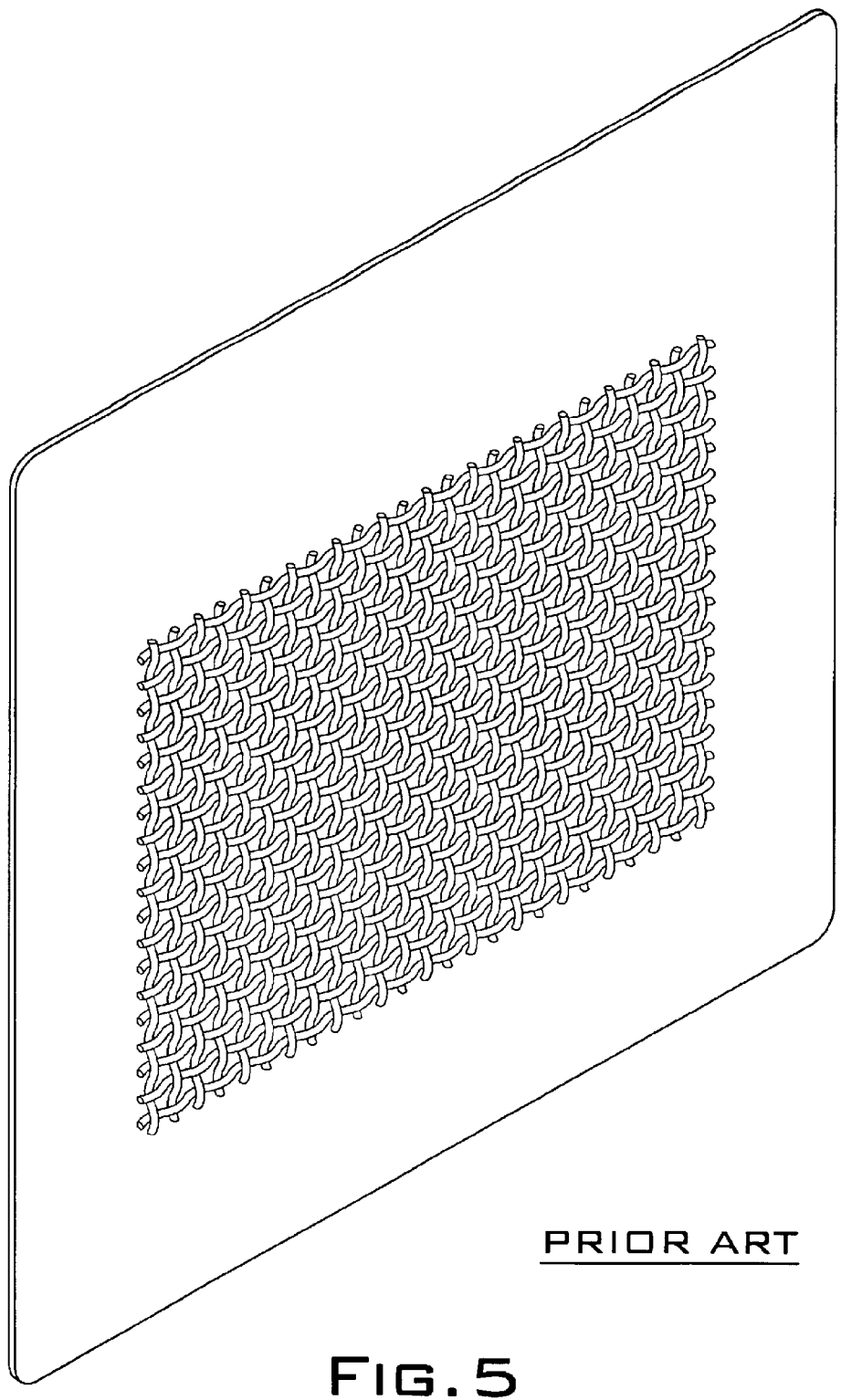
FIG. 5 is an illustration of a prior art plasma generator plate employed with air quality devices in the prior art.
Figure 6:
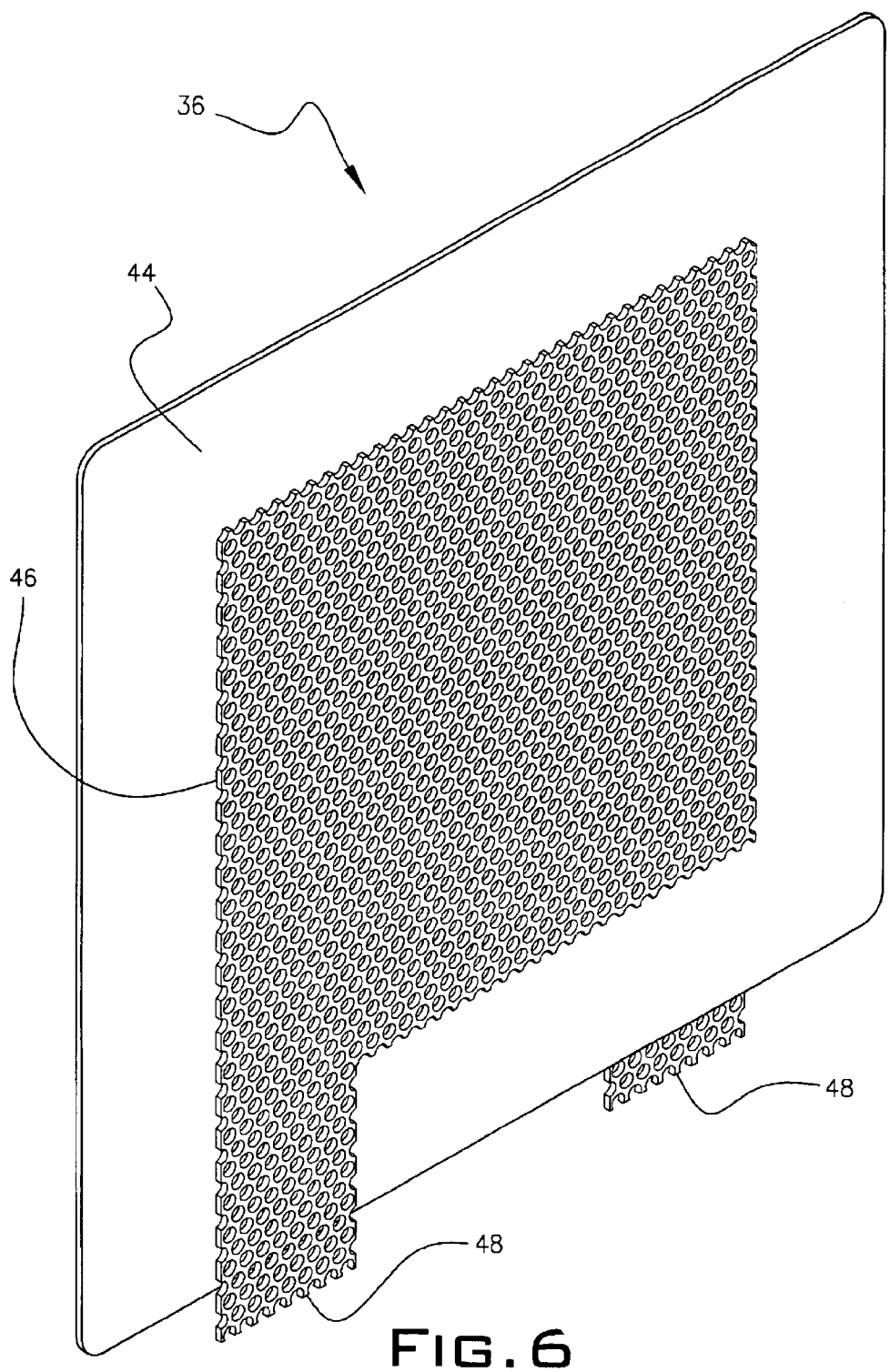
FIG. 6 is an illustration of a preferred cold plasma generator plate employed with the apparatus of the present invention.

As shown in FIG. 6, each generator plate 36 includes a ceramic plate member 44 and a novelly configured screen portion 46 made of perforated steel mounted along opposed sides of plate member 44, each having a tab portion 48 extending downwardly for electrical engagement to generator plate bed 26. The two tab portions 48 for each plate represent a negatively charged cathode and a positively charged anode for each generator plate 36. The unique circular pattern formed on screen portion 46 drastically reduces the formation of "off" gases such as nitric oxide which can form on prior art plates such as the one shown in FIG. 5. In the preferred embodiment, there is approximately 50% open area and 50% closed area on screen potion 46, although other percentages could be employed. Since screen portion 46 of each generator plate 36 rests, in its entirety, against the ceramic plate member 44, no arcing occurs as seen with the prior art plates, again like illustrated in FIG. 5. In the prior art, where wire mesh is typically used for the screen portion, arcing (an open spark) forms due to a gap formed between the surface of the ceramic plate and one of the wires which wraps over the top of the wire beneath it. This arc causes the formation of nitric oxide and heat. Since nitric oxide is catalytic, it can easily destroy the formation of activated oxygen and is therefore not desired. The prior art generator plates typically create a heat build-up and therefore permit the formation of nitric oxide due to the wire mesh on a glass element configuration.

As shown in FIG. 3, plate member 44 engages a pair of connectors 50 extending upwardly from a top surface 52 of generator plate bed 26. In the preferred embodiment, four generator plates 36 are employed and therefore four pair of connectors 50 are provided on generator plate bed top surface 52. However, depending on the application, more or less generator plates 36 could be employed in apparatus 10 of the present invention and therefore more or less connectors 50. If more generator plates 36 are needed, then a larger generator plate bed 26 is employed. This however, results in a need to extend the length of rear housing 14. Although the number of plates can theoretically be an infinite number, preferred embodiments use four to thirteen plates 36.

Generator plates 36 create the activated oxygen used by apparatus 10 through a cold plasma process. The activated oxygen manufactured by the cold plasma generator plates 36 uses only $O_2$ molecules and produces no heat and therefore drastically reduces the production of other harmful "off" gasses. The cold plasma generator plates break the $O_2$ molecule into two single O's without using heat and forces the single O's out through a restricted space encouraging their escape through a crowded magnetic field and therefore reforming (bonding) them into $O_3$ for a short period of time. Heat shortens the life of $O_3$ whereas colder air prolongs its life. Accordingly, the ability to prohibit the creation of heat using the novel generator plates 36 in apparatus 10 is a huge advancement over the prior art. The "cold" in cold plasma is meant as a low electric current versus "hot", a high electrical current which causes arcing. As stated before, arcing causes the formation of heat which in turn influences other gasses to form. The cold plasma process has a regulated electrical leak allowing the high voltage to evenly bleed off, thereby making a very steady and clean $O_3$. In its preferred form, each cold plasma generator plate 36 can produce approximately 0.2 ppm of activated oxygen ($O_3$), although other output amounts can be achieved through the input voltage regulation. In fact, set values can be achieved through switches and voltage regulation if so desired.

Figure 4:
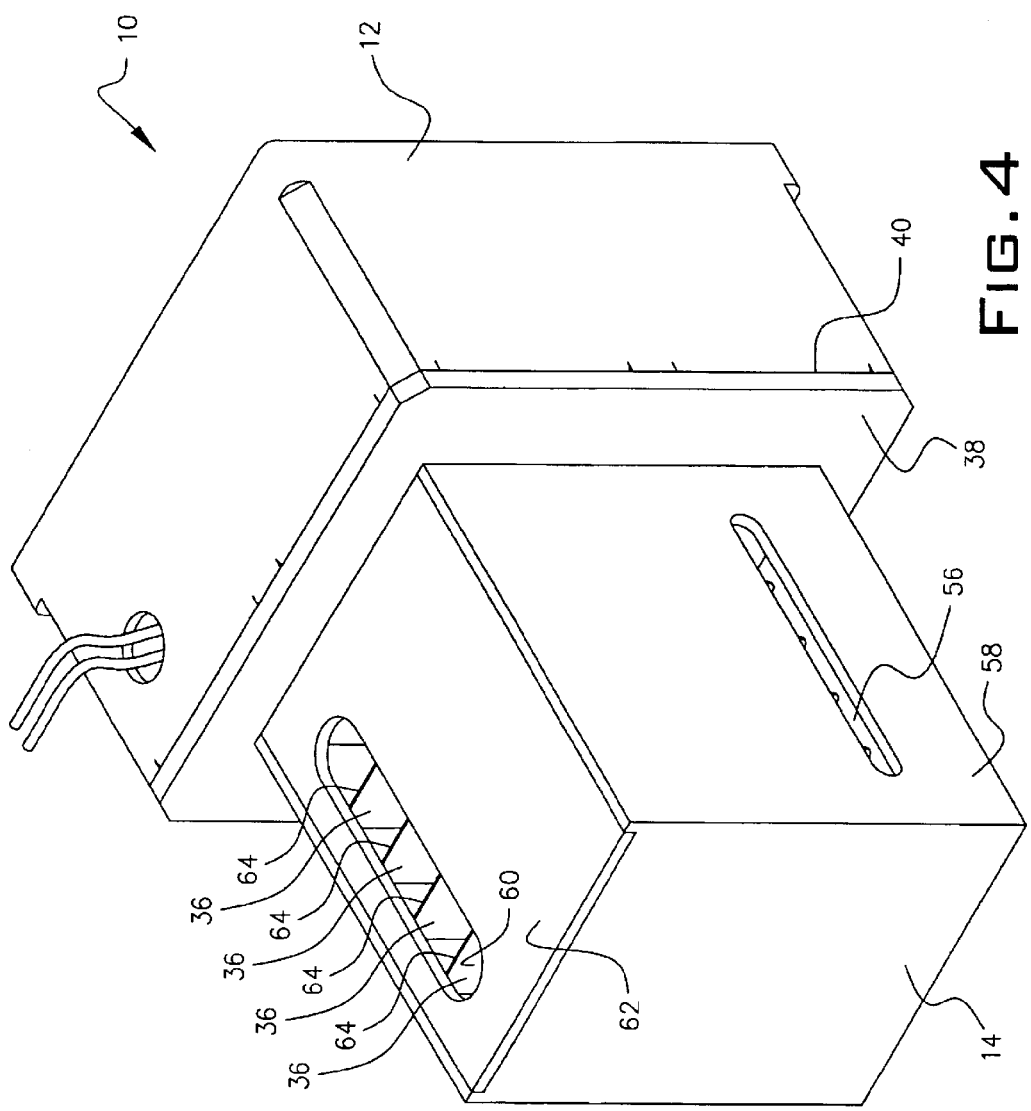
FIG. 4 is a rear perspective view of the apparatus depicted in FIG. 1, illustrating a pair of vents formed in the apparatus rear housing portion.
Figure 7:
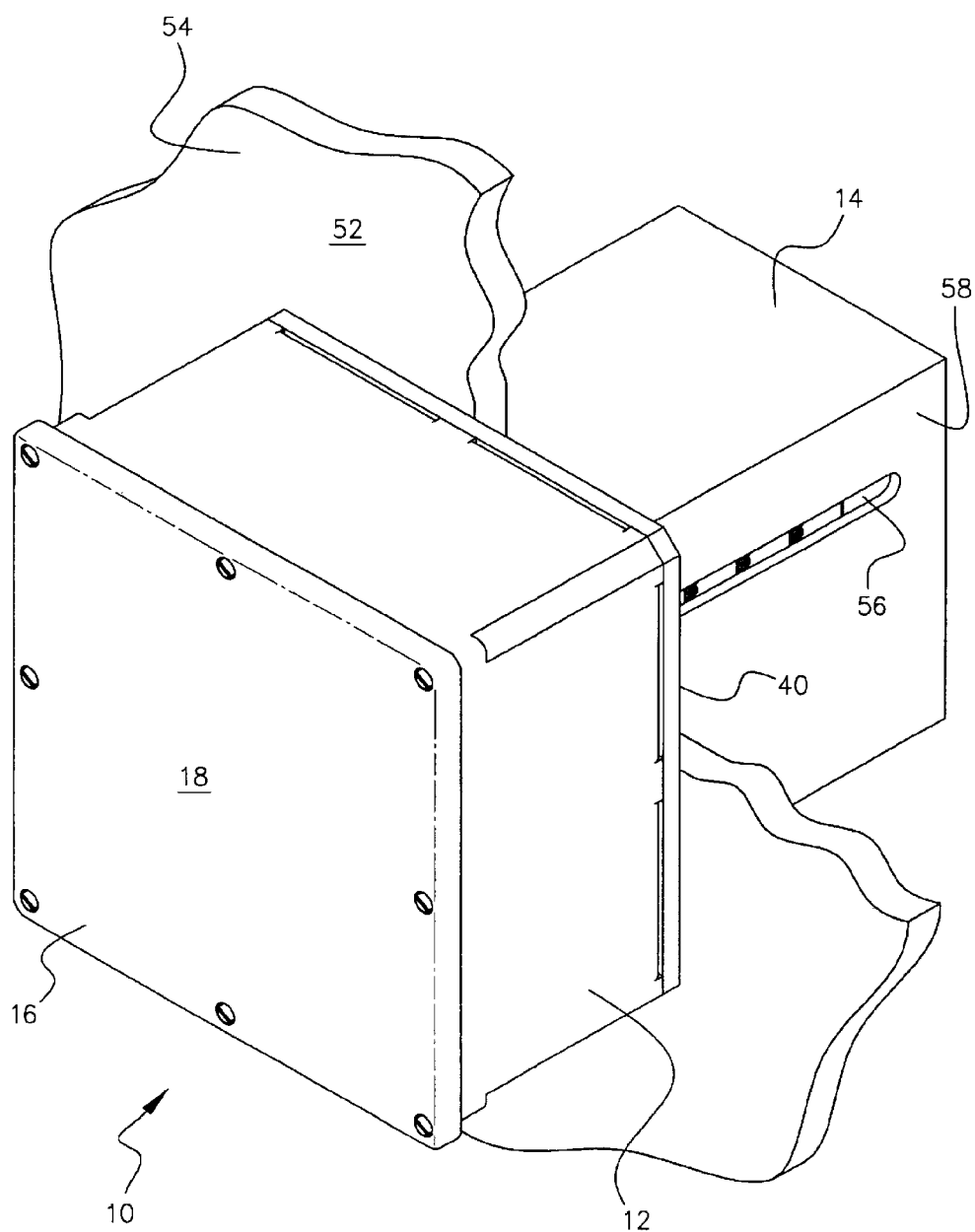
FIG. 7 is a front perspective view of the apparatus of the present invention, mounted within a duct of an HCAV system, the duct being illustrated partially cut-away.

Once the activated oxygen is created, it is introduced to a pressurized air stream and then directed, in its preferred form, through the duct system of an HVAC air system of a building. $O_3$ prefers not to remain in its three oxygen atom form. In fact, it wishes to desperately undo this trio state. When the $O_3$ floats into any environment, one of the atoms looks for a contaminant to attach, if it sees one, it breaks away from the other two oxygen atoms. The attack on the contaminant creates an explosion whereby both the contaminant and the single "break-away" oxygen atom are destroyed. This leaves the other two oxygen atoms behind thereby providing pure oxygen ($O_2$) without the presence of the contaminant. Typically the explosion changes the contaminant into carbon dioxide and hydrogen which can be safely inhaled by humans and other animals and does not appear to adversely effect humans or other animals in any harmful manner. If the $O_3$ can not find a contaminant in its environment to destroy, it will eventually attack itself and change it's configuration back to $O_2$ in 20 to 30 minutes at ambient room temperature. In higher temperature environments, it will change back more rapidly, whereas in colder environments, it will change back more slowly, As stated before, in the preferred embodiment, apparatus 10, as shown in FIGS. 1–4 and FIG. 7, is installed within the air duct of an HVAC system, preferably on the supply side of the air handler (not shown). Rear housing 14 inserts within the air duct whereas front housing 12 rests against an outer wall 52 of an air duct 54 as illustrated in FIG. 7. The exposed portions of the layer of insulating foam 40 mounted on front housing backside 38 lays flush or juxtaposed against air duct outer wall 52. As shown in FIGS. 3 and 4, a pair of air vents 56 are formed in rear housing 14. An intake air vent 56 is formed along a lower portion 58 of rear housing 14, proximal to generator plate bed 26, and receives the pressurized air flow moving from the fan of the HVAC system air handler. This pressurized air mixes with the cold plasma generated activated oxygen formed within the internal cavity 34 of the apparatus rear housing 14 which thereafter exits through an exhaust air vent 60 formed in a lid portion 62 of rear housing 14 proximal to a top end 64 of the generator plates 36 enclosed therewithin. In its preferred form, intake air vent 56 is smaller in area than exhaust air vent 60.

To install the preferred apparatus 10, a square shaped opening is cut through an air duct outer wall of an HVAC system. A pair of notches are cut at opposed sides of the opening to accommodate a pair of screws. A support frame (not shown) made of metal can be inserted within the cut opening and is held in place with metal tape. Rear housing 14 is thereafter inserted into the cut opening until insulating foam 40 rests against air duct outer wall 52 as shown in FIG. 7, secured with the screws. If apparatus 10 employs more than four generator plates 36 and therefore necessitates a larger length rear housing 14, a shroud (not shown) can be employed around a front portion of the rear housing 14 to stabilize apparatus 10 in the HVAC air duct due to its increased weight towards the back of apparatus 10. Lid 18 is removable so that access can be given to the electrical components within front housing 12. Thereafter, apparatus 10 is connected to its power source or supply voltage junction box.

Figure 8:
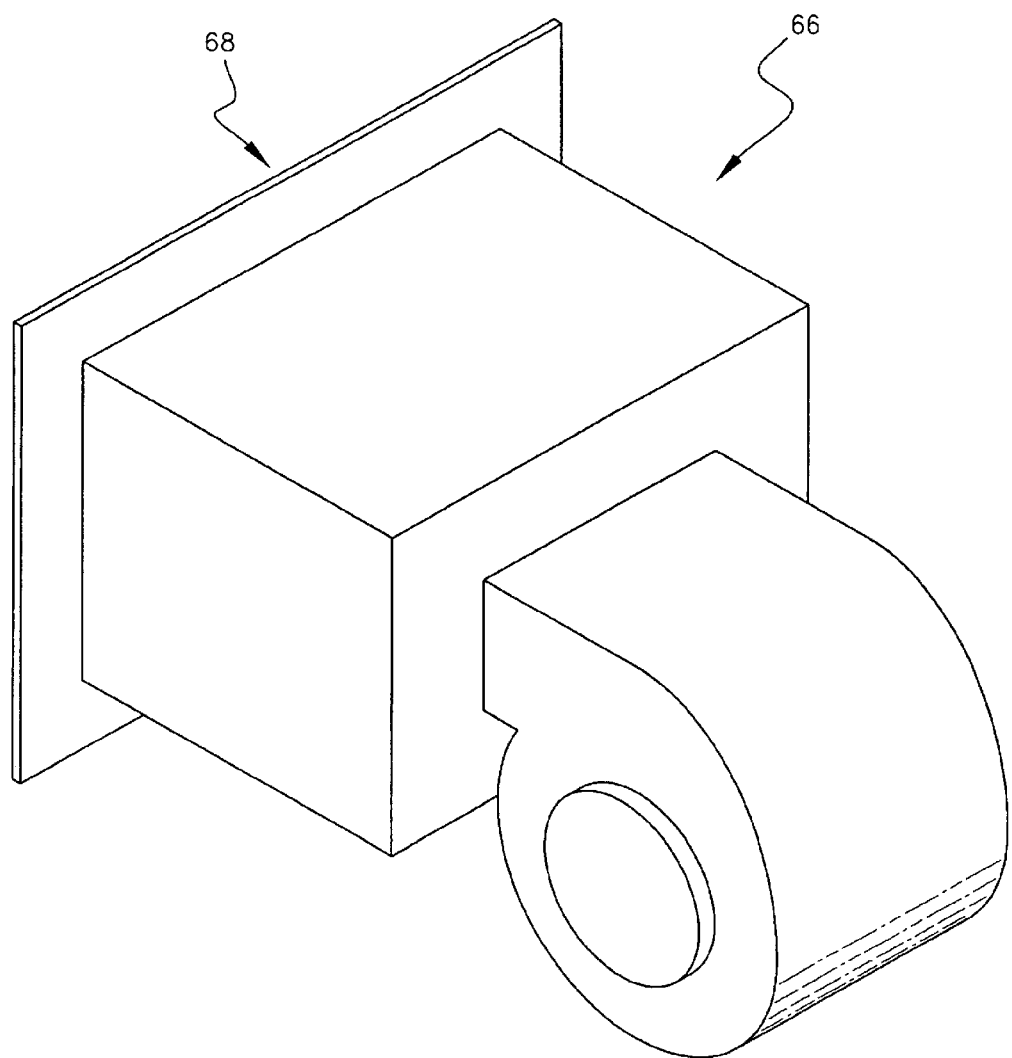
FIG. 8 is a rear perspective view of a first alternate embodiment of the apparatus of the present invention mounted to an air vent of a building hallway corridor.
Figure 9:
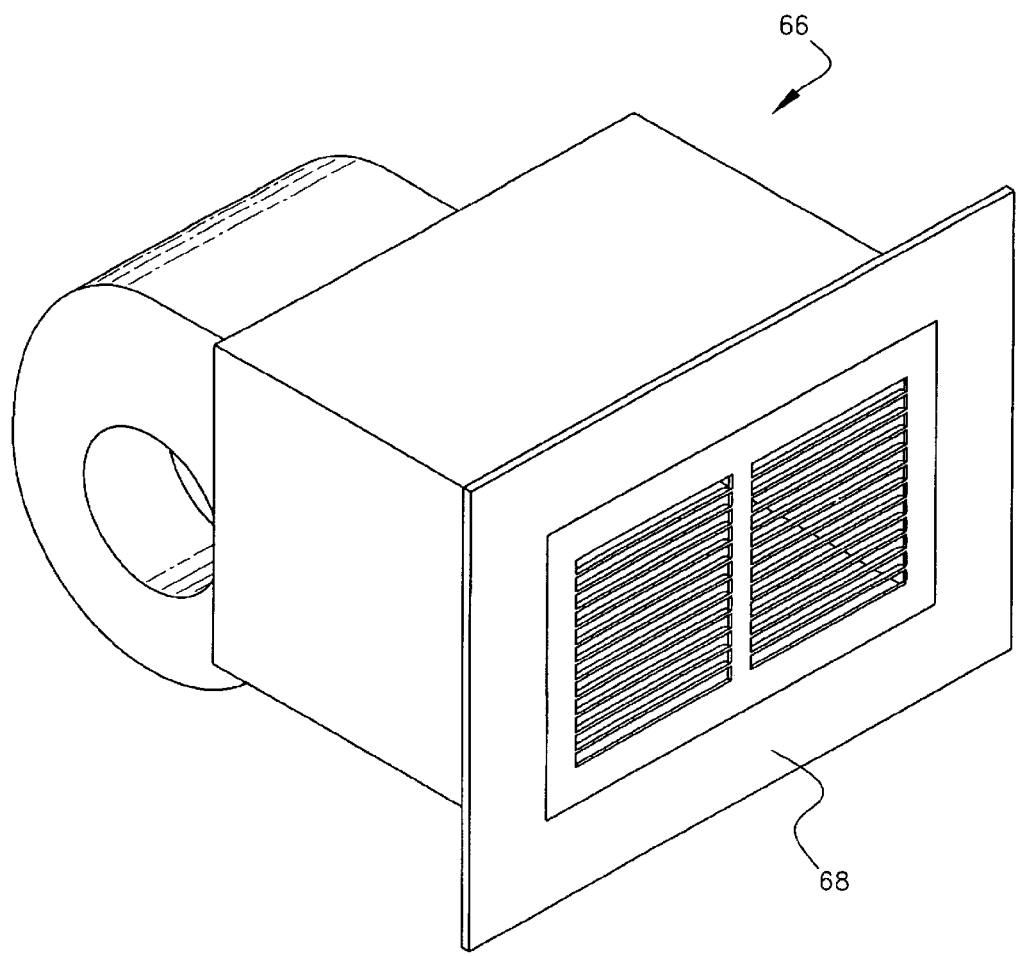
FIG. 9 is a front perspective view of the first alternate embodiment of the apparatus of the present invention mounted to an air vent of a building hallway corridor.

Referring to FIGS. 8 and 9, a first alternate embodiment apparatus 66 is shown. Apparatus 66 is typically installed along a hallway corridor by attaching apparatus 66 to an air vent 68 (FIG. 9). Apparatus 66 contains the same circuitry (although not shown) as that of the preferred apparatus 10. Accordingly, a set of generator plates are mounted to a generator plate bed which is electrically coupled to a transformer which is powered by a power source. A pressure control switch ensures the unit operates in the presence of a pressurized air source (i.e., a fan operating). The fan (not shown) draws air into apparatus 66 and mixes it with the activated oxygen ($O_3$). The pressurized activated oxygen is then pushed out through the air vent 68 into the building corridor. Again, the pressurized air assists in prohibiting contaminants from entering the building being treated with apparatus 66. This first alternate embodiment would typically be installed in older buildings not having a central HVAC air system. The fan and other electrical components can be powered through a connection to a 110 volt AC plug or other known readably available power sources.

Figure 10:
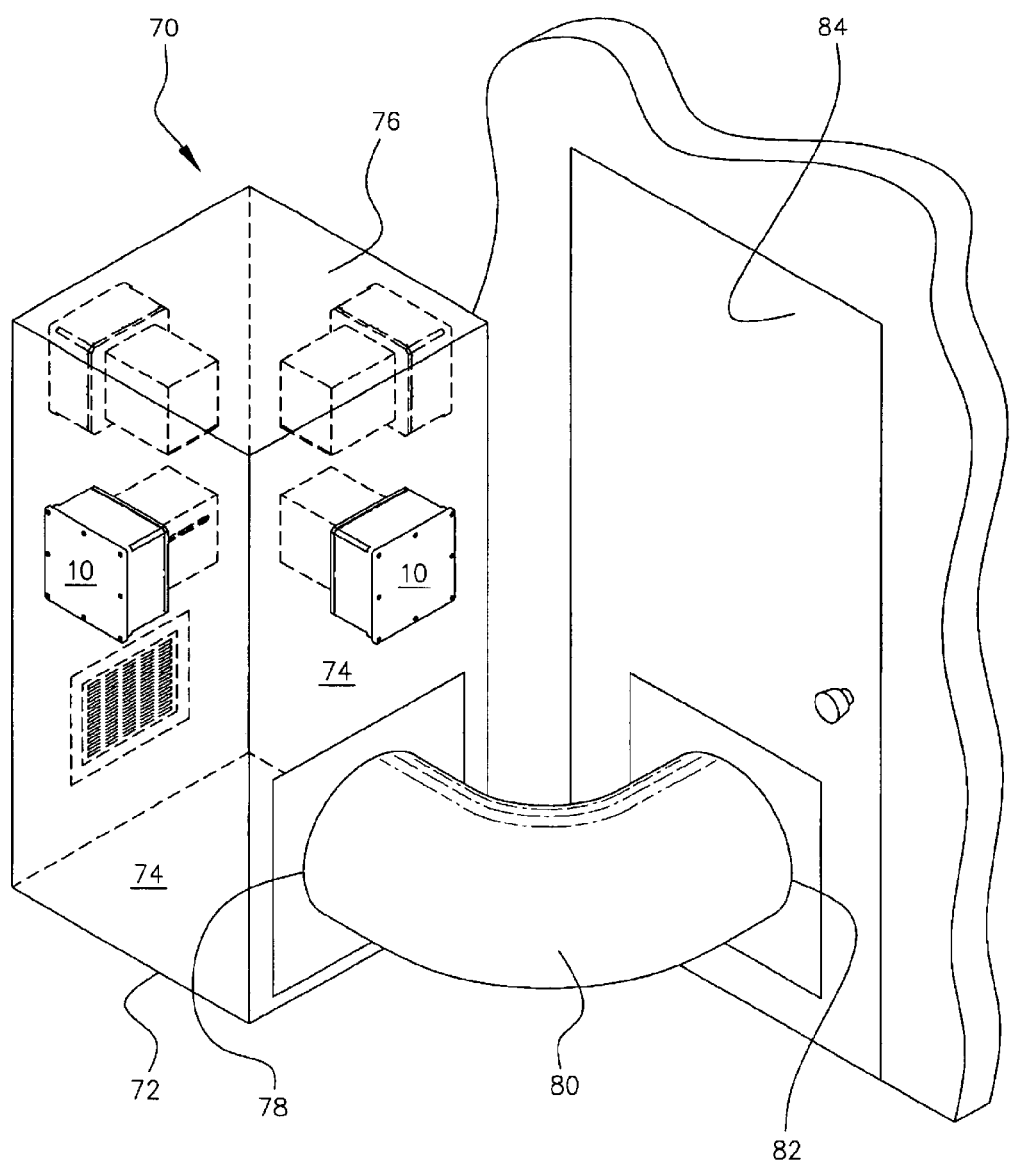
FIG. 10 is a perspective view of a second alternate embodiment of the apparatus of the present invention illustrating how a stand alone unit can be employed to treat an enclosed environment wherein the apparatus is not connected to the HVAC system of the enclosed environment.

Referring to FIG. 10, a second alternate embodiment is shown as a "stand alone" unit 70. Unit 70 encloses a plurality of individual apparatuses 10. The preferred embodiment for unit 70, employs four apparatuses 10. As shown, unit 70 is rectangular in shape and includes a bottom end 72 which supports unit 70 upon a ground surface. Unit 70 is typically used in an enclosed environment, such as an office building, for the purpose of treating a contaminated area. For instance, an area which has been exposed to a contaminant which would be harmful to humans to inhale for any period of time could employ unit 70 to cleanse the environment of the contaminant. The square footage of the area to be treated would dictate the number of apparatus 10 to be used with unit 70 and the total number of units 70 that could be employed within one environment. As stated before, the preferred unit 70 employs four apparatuses 10, wherein one each are attached to side walls 74 of unit 70. A top wall 76 is also employed. Unit 70 further includes an inlet port 78 by which a tubular member 80 attaches thereto and extends to an opening 82 to the outside ambient air, typically through a sealed doorway 84, as illustrated in FIG. 10. A fan (not shown) is installed in front of the tubular member inside unit 70. Unit 70 further includes an exit port by which the pressurized $O_3$ created by the plurality of apparatuses 10 and the fan can be expelled into the environment to be treated.

Equivalent elements can be substituted for the ones set forth above such that they perform the same function in the same way for achieving the same result.

Having thus described the invention what is claimed and desired to be secured by Letters Patent is:

1. A biological and chemical defense apparatus for the treatment of an enclosed environment utilizing cold plasma generated pressurized activated oxygen, the apparatus comprising:

a) at least one housing having an internal cavity;

b) at least one cold plasma generator plate having an anode and a cathode, the at least one generator plate creating the activated oxygen;

c) a generator plate bed enclosed within the at least one housing electrically coupled to the at least one generator plate;

d) at least one air inlet port formed in the at least one housing for drawing ambient air into the internal cavity;

e) an air exit port formed in the at least one housing for expelling the pressurized activated oxygen from the at least one housing;

f) electrical charging means coupled to the generator plate bed for supplying an electrical charge to the at least one generator plate;

g) control switching means for energizing the electrical charging means; and h) a power source coupled to the control switching means and the electrical charging means.

2. The biological and chemical defense apparatus of claim 1, wherein a pair of housings are employed, a front housing having a first internal cavity enclosing the electrical charging means and the control switching means and a rear housing having a second internal cavity enclosing the generator plate bed and the at least one generator plate, the front and rear housings mounted juxtaposed to one another.

3. The biological and chemical defense apparatus of claim 2, further comprising a layer of insulating foam inserted between the front and rear housings.

4. The biological and chemical defense apparatus of claim 2, wherein the at least one air inlet port and the air exit port are formed in the rear housing along different sides walls of the rear housing.

5. The biological and chemical defense apparatus of claim 4, wherein the apparatus is inserted within an air duct system of an HVAC air system such that the rear housing is enclosed and sealed within the air duct system and the front housing extends outwardly from an outer wall of the air duct.

6. The biological and chemical defense apparatus of claim 1, wherein the at least one generator plate comprises a generally flat plate member having opposing side faces, each side face having a generally flat layer of screening mounted thereupon.

7. The biological and chemical defense apparatus of claim 6, wherein the at least one generator plate further comprises a pair of downwardly extending tabs, a first tab comprising the anode and a second tab comprising the cathode of the at least one generator plate, the anode and cathode providing the electrical coupling to the generator plate bed.

8. The biological and chemical defense apparatus of claim 1, wherein a low level current is applied to the at least one generator plate through the generator plate bed from the electrical charging means which causes the at least one generator plate to create the activated oxygen.

9. The biological and chemical defense apparatus of claim 1, wherein the activated oxygen comprises a gas having a molecular structure of three oxygen atoms.

10. The biological and chemical defense apparatus of claim 1, wherein the generator plate bed comprises at least one pair of connectors for electrically coupling the at least one generator plate to the generator plate bed.

11. The biological and chemical defense apparatus of claim 1, wherein the electrical charging means is a transformer and the control switching means is a pressure control switch having an air inlet port and an air outlet port, the pressure control switch reacting to an increase in an air pressure level above that of ambient air surrounding the apparatus.

12. The biological and chemical defense apparatus of claim 1, wherein four generator plates are employed.

13. The biological and chemical defense apparatus of claim 1, further comprising a fan mounted proximal to the air inlet port formed in the at least one housing.

14. The biological and chemical defense apparatus of claim 1, wherein the at least one housing comprises a plurality of housings mounted within a larger secondary housing, the secondary housing having a fan, an air inlet port and an air exhaust port, the fan mounted in front of the air inlet port within the secondary housing, the air inlet port attached to a tube which extends to a sealed opening to an outer environment separate from that of the environment in which the secondary housing is located, the air exhaust port expelling the pressurized activated oxygen created within the secondary housing by the fan and the plurality of housings.

15. The biological and chemical defense apparatus of claim 1, wherein the at least one air inlet port has a smaller area than the air exit port.

16. A biological and chemical defense apparatus for the treatment of an enclosed environment utilizing cold plasma generated pressurized activated oxygen, the apparatus comprising:
   a) at least one pair of housings comprising a front and rear housing mounted juxtaposed to one another, each housing of the at least one pair of housings having an internal cavity;
   b) at least one cold plasma generator plate having an anode and a cathode, the at least one generator plate creating the activated oxygen;
   c) a generator plate bed enclosed within the internal cavity of the rear housing of the at least one pair of housings electrically coupled to the at least one generator plate;
   d) an air inlet port formed in the rear housing of the at least one pair of housings for drawing ambient air into the rear housing internal cavity;
   e) an air exit port formed in the rear housing of the at least one pair of housings for expelling the pressurized activated oxygen from the at least one housing;
   f) electrical charging means coupled to the generator plate bed for supplying an electrical charge to the at least one generator plate;
   g) control switching means for energizing the electrical charging means; and
   h) a power source coupled to the control switching means and the electrical charging means.

17. The biological and chemical defense apparatus of claim 16, wherein the front housing internal cavity encloses the electrical charging means and the control switching means and the rear housing internal cavity encloses the generator plate bed and the at least one generator plate.

18. The biological and chemical defense apparatus of claim 16, further comprising a layer of insulating foam inserted between the front and rear housings.

19. The biological and chemical defense apparatus of claim 16, wherein the at least one generator plate comprises a generally flat plate member having opposing side faces, each side face having a generally flat layer of screening mounted thereupon.

20. The biological and chemical defense apparatus of claim 19, wherein the at least one generator plate further comprises a pair of downwardly extending tabs, a first tab comprising the anode and a second tab comprising the cathode of the at least one generator plate, the anode and cathode providing the electrical coupling to the generator plate bed.

21. The biological and chemical defense apparatus of claim 16, wherein a low level current is applied to the at least one generator plate through the generator plate bed from the electrical charging means which causes the at least one generator plate to create the activated oxygen.

22. The biological and chemical defense apparatus of claim 16, wherein the activated oxygen comprises a gas having a molecular structure of three oxygen atoms.

23. The biological and chemical defense apparatus of claim 16, wherein the generator plate bed comprises at least one pair of connectors for electrically coupling the at least one generator plate to the generator plate bed.

24. The biological and chemical defense apparatus of claim 16, wherein the apparatus comprises one pair of housings and is inserted within an air duct system of an HVAC air system such that the rear housing is enclosed and sealed within the air duct system and the front housing extends outwardly from an outer wall of the air duct.

25. The biological and chemical defense apparatus of claim 16, wherein the electrical charging means is a transformer and the control switching means is a pressure control switch having an air inlet port and an air outlet port, the pressure control switch reacting to an increase in an air pressure level above that of ambient air surrounding the apparatus.

26. The biological and chemical defense apparatus of claim 16, wherein one pair of housings is employed, the rear housing of the one pair of housings including a fan mounted proximal to the air inlet port formed in the rear housing.

27. The biological and chemical defense apparatus of claim 16, wherein the at least one pair of housings comprises a set of four pair of housings, each pair of housings mounted along side walls of a larger secondary housing such that the rear housing of each pair of housings is enclosed and sealed within the larger secondary housing and the front housing of each pair of housings extends outwardly from an outer wall of the secondary housing side walls, the secondary housing having a fan, an air inlet port and an air exhaust port, the fan mounted in front of the air inlet port within the secondary housing, the air inlet port attached to a tube which extends to a sealed opening to an outer environment separate from the environment in which the secondary housing is located, the air exhaust port expelling the pressurized activated oxygen created within the secondary housing by the fan and the four pair of housings.

28. A biological and chemical defense apparatus for the treatment of an enclosed environment utilizing cold plasma generated pressurized activated oxygen, the apparatus comprising:
   a) a front and rear housing mounted juxtaposed to one another, each housing having an internal cavity;
   b) at least one cold plasma generator plate having an anode and a cathode, the at least one generator plate creating the activated oxygen;
   c) a generator plate bed enclosed within the internal cavity of the rear housing of the at least one pair of housings electrically coupled to the at least one generator plate;
   d) an air inlet port formed in the rear housing for drawing ambient air into the rear housing internal cavity;
   e) an air exit port formed in the rear housing for expelling the pressurized activated oxygen from the rear housing;
   f) electrical charging means coupled to the generator plate bed for supplying an electrical charge to the at least one generator plate;
   g) control switching means for energizing the electrical charging means; and
   h) a power source coupled to the control switching means and the electrical charging means.

* * * * *